United States Patent [19]

Miura et al.

[11] Patent Number: 5,723,771

[45] Date of Patent: Mar. 3, 1998

[54] VIBRATORY LIQUID DETECTOR

[75] Inventors: Shinsuke Miura, Mishima; Norihiko Kumagai; Kenji Muraoka, both of Tokyo, all of Japan

[73] Assignee: Yamaichi Electronics Co., Ltd., Tokyo, Japan

[21] Appl. No.: 847,340

[22] Filed: Apr. 23, 1997

Related U.S. Application Data

[63] Continuation of Ser. No. 614,475, Mar. 13, 1996, abandoned.

[30] Foreign Application Priority Data

Mar. 13, 1995 [JP] Japan ................................ 7-081846

[51] Int. Cl.⁶ .................................................. G01N 11/10
[52] U.S. Cl. ........................................................ 73/54.24
[58] Field of Search ............................. 73/54.24, 54.25, 73/54.26, 54.27

[56] References Cited

U.S. PATENT DOCUMENTS

| | | | |
|---|---|---|---|
| 3,062,040 | 11/1962 | McKennel et al. | 73/54.24 |
| 3,382,706 | 5/1968 | Fitzgerald et al. | 73/54.25 |
| 3,712,117 | 1/1973 | Fitzgerald et al. | 73/54.26 |
| 4,558,588 | 12/1985 | Beaudoin et al. | 73/54.25 |
| 4,566,181 | 1/1986 | Matusik et al. | 73/54.25 X |
| 4,857,792 | 8/1989 | Miura et al. | 310/323 |
| 4,909,068 | 3/1990 | Miura et al. | 73/32 A |
| 5,596,139 | 1/1997 | Miura et al. | 73/54.24 |
| 5,621,165 | 4/1997 | Miura et al. | 73/54.27 |

*Primary Examiner*—Michael Brock
*Attorney, Agent, or Firm*—Wenderoth, Lind & Ponack

[57] ABSTRACT

A vibratory liquid detector which includes a detecting element secured to a free end of a vibration transmission shaft. The detector is suspended in a liquid and receives vibration from the vibration transmission shaft. A spring member supports the vibration transmission shaft and has a fixed end, secured to an intermediate portion of the vibration transmission shaft, and a free end located at a position spaced apart from the periphery of the vibration transmission shaft. The free end is also axially spaced from the fixed end, and includes a support part supporting the whole detecting unit. The spring member provides satisfactory elasticity with respect to torsional vibrations of the vibration transmission shaft between the fixed and the free ends, thus permitting adequate vibrational energy transmission from the vibrator to the detecting element via the vibration transmission shaft.

3 Claims, 3 Drawing Sheets

VIBRATORY LIQUID DETECTOR

This application is a continuation of now abandoned application, Ser. No. 08/614,475, filed Mar. 13, 1996.

BACKGROUND OF THE INVENTION

Field of the Invention

This invention relates to a vibratory liquid detector, which is used for measuring the viscosity, density, liquid level, etc. of a liquid. The detector includes a detecting element which is dipped in a liquid and vibrated by a circular vibrator of a piezoelectric ceramic material or the like. U.S. Pat. No. 4,857,792 and U.S. Pat. No. 4,909,068 disclose a detecting element directly coupled to a vibration transmission shaft which is in turn directly coupled to a circular vibrator. Vibrations of the vibrator are transmitted to the detecting element via the vibration transmission shaft.

The vibrating unit has to be insulated vibration-wise from a casing accommodating the vibrator or from a liquid vessel in which the detecting element is dipped or from a liquid passage pipe, on which the vibrating unit is mounted. In the prior art vibrating unit, an inertial mass is provided on the end of the unit opposite the detecting element. The inertial mass is suspended from the casing via rubber or a similar buffering material.

However, in order to suspend the vibrating unit (i.e., upper end of the vibrator) from the casing via the inertial mass, the inertial mass has to be considerably large in weight and large in size in comparison to the weight of the whole vibrating unit. The whole unit, therefore, has to be heavy in weight and large in size.

In addition, while the prior art unit meets the requirement that it is suspended such that it is insulated vibration-wise, the inertial mass which is directly coupled to the casing, rigidly restricts (i.e., secures in position) the vibrating element undergoing torsional vibrations, and therefore this structure is a cause of external disturbances which make it difficult to obtain stable and sound torsional vibrations.

The above problems are also posed in the case where the vibrating unit is supported by a liquid vessel or pipe for steady-state measurements of the viscosity or density of a liquid, in which the detecting element is suspended.

SUMMARY OF THE INVENTION

The invention seeks to solve the above problems, and its object is to provide a vibratory liquid detector, in which a vibrating unit is supported by a spring member on a casing or a vessel such that it is insulated vibration-wise from the casing or vessel. The spring member is disposed on the vibration transmission shaft, preferably near a vibration node thereof, such as to support the vibration transmission shaft. The spring member has a fixed and secured to an intermediate portion of the vibration transmission shaft and a free end located at a position spaced apart from the periphery of the vibrating transmission shaft and also spaced axially from the fixed end. The free end has a support part which supports the whole vibrating unit.

Another object of the invention is to provide a vibratory liquid detector, in which the spring member is a cylindrical member capable of torsional vibrations about its axis. The spring member has one end as the fixed end and the other end as the free end.

According to the invention, it is possible to adopt a structure, in which the whole vibrating unit is suspended by mounting the fixed end of the spring member at the vibration node point of the vibration transmission shaft. The shaft is capable of torsional vibrations as the free end of the spring member is connected to the casing or liquid vessel. The unit thus has freely vibrating ends. In this structure, the spring member has satisfactory elasticity with respect to the torsional vibrations of the vibration transmission shaft between the fixed end, secured to an intermediate portion of the vibration transmission shaft, and the free end located at a position spaced apart from the periphery of the vibration transmission shaft and also axially spaced from the fixed end. The spring member permits adequate vibration energy transmission from the vibrator via the vibration transmission shaft to the detecting element.

It is further possible to provide a highly reliable liquid detector, which can promote active, steady and highly efficiency resonance of two portions of the unit on either side of the fixed end of the spring member. In addition, the vibrating unit can be firmly secured to a casing, a liquid vessel, or a pipe by means of the support part that is formed at the free end of the spring member. Even with the vibrating unit secured firmly in this way, the transmission of vibrations is not adversely affected, and it is possible to obtain highly reliable measurements by excluding external disturbances caused by the suspension of the unit.

DETAILED DESCRIPTION OF THE PREFERRED EMBODIMENT

An embodiment of the invention will be described with reference to FIGS. 1 to 6.

Figure 1:
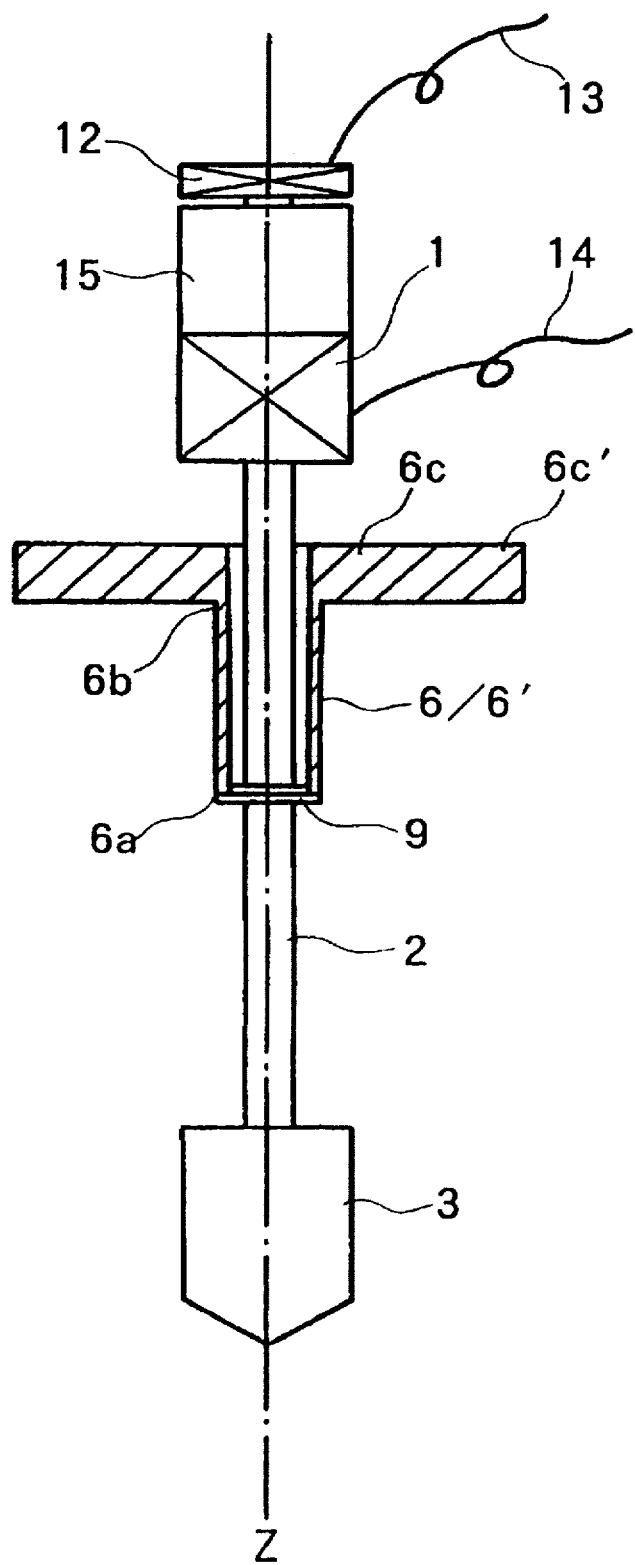
FIG. 1 is a side view, partly in section, showing an embodiment of a vibratory liquid detector according to the present invention.

A vibrator 1, which is capable of undergoing circular vibrations (or torsional vibrations) about its vibration axis Z, is shown in FIG. 1. A vibration transmission shaft 2, the axis of which coincides with a circular vibration axis Z, is directly coupled to the vibrator 1. A detecting element 3 which also has an axis which coincides with the vibration axis Z, is directly coupled to a free or unsupported end of the vibration transmission shaft 2. The vibrator 1, vibration transmission shaft 2 and detecting element 3 constitute a vibrating unit, in which the detecting element 3 is vibrated with circular vibrations by the vibrator 1. The vibration transmission shaft 2 is adapted such that its two portions, on the opposite sides of a resonance node O, undergo circular vibrations in opposite directions, that is, the shaft 2 undergoes torsional vibrations as a whole about the node O.

The vibration transmission shaft 2 may be a cylindrical member, a polygonal member, a plate-like member, a block-like member or any combination of these members so long as it is a member which is suitable for transmitting vibrations, undergoing torsional vibrations and permitting resonance of the vibrator 1 and detecting element 3.

The vibrator 1 and detecting element 3 are disposed such that the detecting element 3 undergoes circular vibrations when the vibrator 1 generates circular vibrations about the axis Z. The vibration transmission shaft 2 induces torsional vibrations about the vibration node O, and the vibrations from the vibrator 1 are thus transmitted to the detecting element 1. The detecting element 3 is suspended in a liquid 10 to be measured in order to detect viscosity resistance, inertial mass, etc. of the liquid 10.

Figures 2, 3:
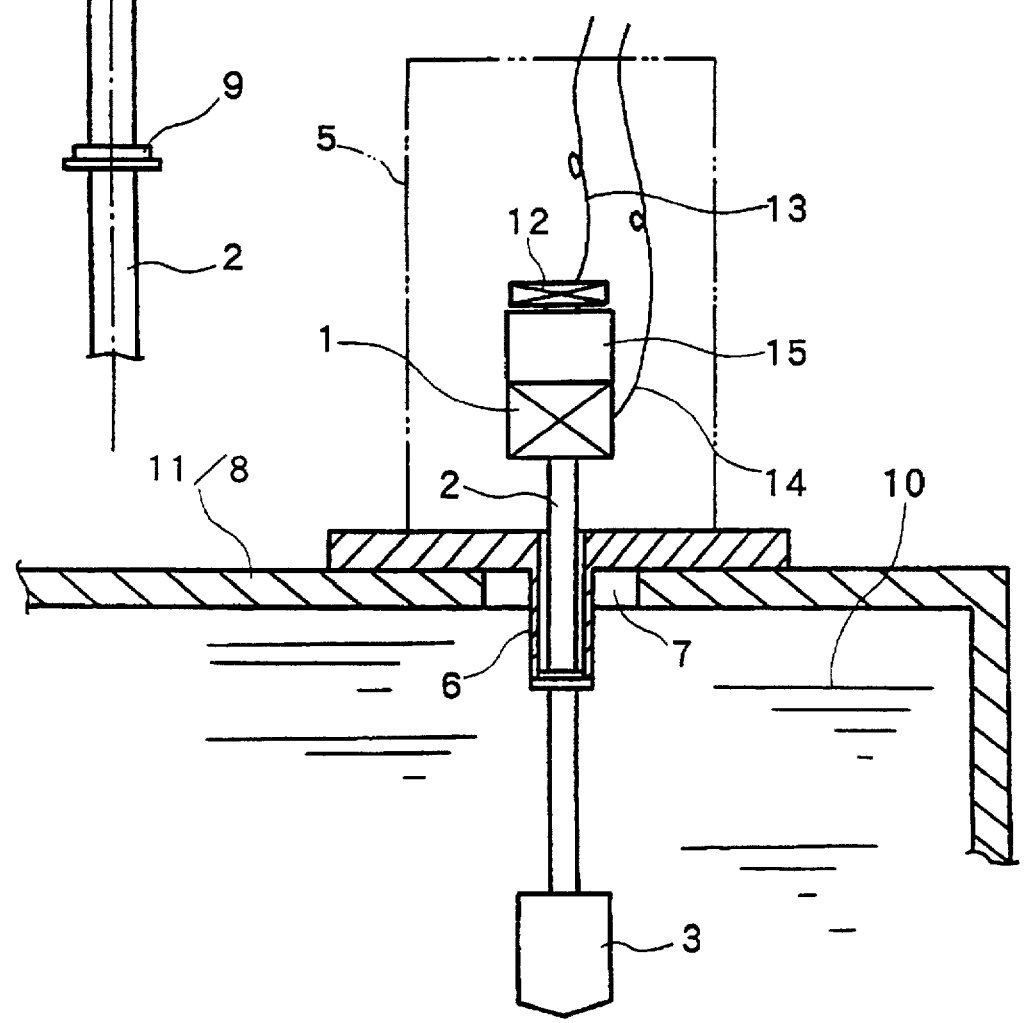
FIG. 2 is an exploded sectional view showing a spring member of the detector.
FIG. 3 is a fragmentary sectional view showing an example of a suspending structure for the detector.
Figure 6:
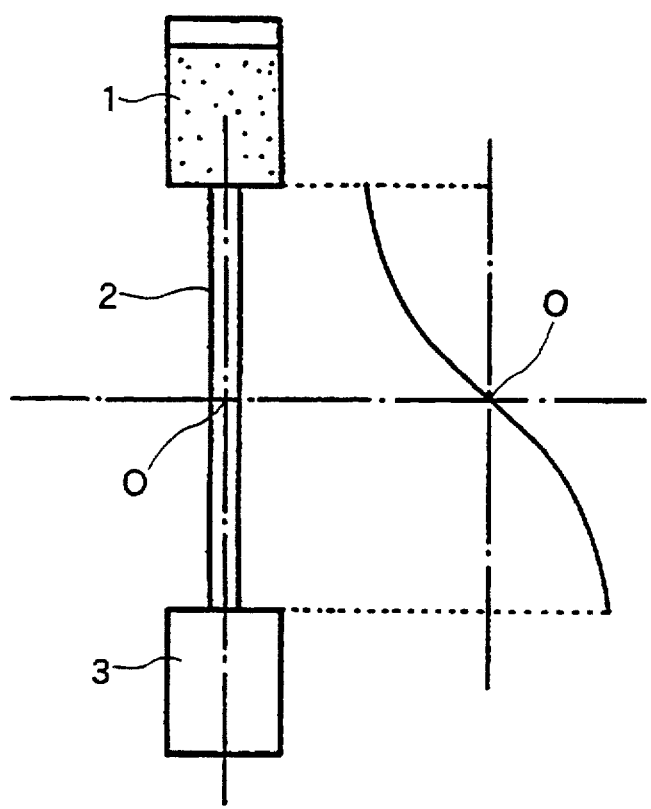
FIG. 6 is a graph for illustrating a mode of resonance between a vibrator and the detecting element.

The vibrator 1 may be a torsional vibrator such as the type shown in FIGS. 6 and 7 of Japanese Patent Publication No. 5-20692 or a torsional vibrator such as the type shown in FIG. 3 or FIGS. 9 and 10 of Japanese Patent Publication No. 5-20693. These vibrators can cause the vibration transmission shaft 2 and detecting element 3 to undergo circular vibrations about the axis Z.

The vibrator 1 and an upper portion of the vibration transmission shaft 2 extending from the vibrator 1, are accommodated in a casing 5, while a lower portion of the vibration transmission shaft 2 and the detecting element 3, directly coupled to the lower portion, extend outwardly from an opening 7 in the casing 5.

Figure 4:
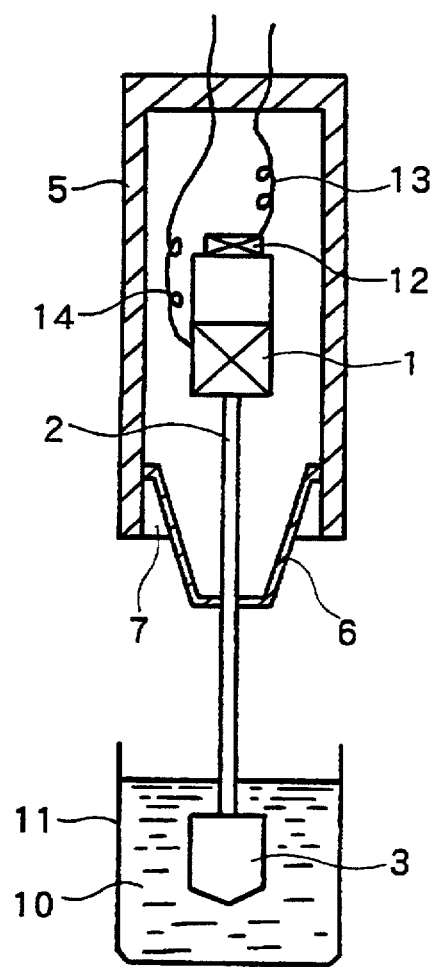
FIG. 4 is a sectional view showing another example of a suspending structure for the detector.

A spring member 6 is mounted on the vibration transmission shaft 2, on a portion of the shaft which includes or is near the vibration node O. The spring member 6 serves as a means for supporting the vibration unit in a suspended state from the casing 5 as shown in FIG. 4. Also, the spring member 6 serves as a means for suspending the vibrating unit from a vessel 11 for accommodating a liquid to be measured or from a pipe outer wall 8, as shown in FIG. 3. The spring member 6 has an end 6a which is fixed or secured to an intermediate portion of the vibration transmission shaft 2 and a free end 6b located at a position spaced apart from the periphery of the vibration transmission shaft 2 and also axially spaced from the fixed end 6a. The end 6b has a support part 6c which supports the detector.

The spring member 6 is, for example, a cylindrical member 6', which has one end as the fixed end 6a and the other end as the free end 6b. The cylindrical member 6', as shown in FIGS. 1 to 3, is disposed concentrically with the vibration transmission shaft 2 and has, for instance, its lower end as the fixed end 6a and its upper end as the free end 6b. Alternatively, although not shown, the cylindrical member 6' may have the upper end as fixed end 6a and the lower end as the free end 6b.

The intermediate portion of the vibration transmission shaft 2 has a concentric flange 9. The intermediate portion includes or is near the vibration node O. The lower or upper open end of the cylindrical member 6' is fittedly secured (for instance welded) to the flange 9, thus forming the fixed end 6a. Alternatively, the vibration transmission shaft 2 may be inserted into a hole formed in the lower or upper end of the cylindrical member 6' in close contact therewith so as to be secured thereto, thus forming the fixed end 6a. The cylindrical member 6' is truly cylindrical, or conically flares toward the free end 6b. The support part 6c is formed at the free end 6b of the cylindrical member 6' as shown in FIGS. 1 to 3. In this example, the cylindrical member 6' is integral with the flange-like support part 6c', which is mounted on a wall at the opening 7 so as to seal the opening. The whole vibrating unit is suspendedly supported on the vessel 11 or from casing 5. The vibration transmission shaft 2 thus penetrates the opening 7 with the detecting element 3 suspended outside of the casing 5 in the liquid 10. Both ends of the shaft, on the vibrator side and on the detecting element side, are thus free ends. The cylindrical member 6' is made of a metal such as stainless steel, titanium, etc. It is also possible to use a synthetic resin cylindrical member. The cylindrical member 6' as the spring member 6 serves both as the suspending means and as a lid member mounted on the vessel 11 or casing 5 to prevent leakage of liquid through the opening 7.

Figure 5:
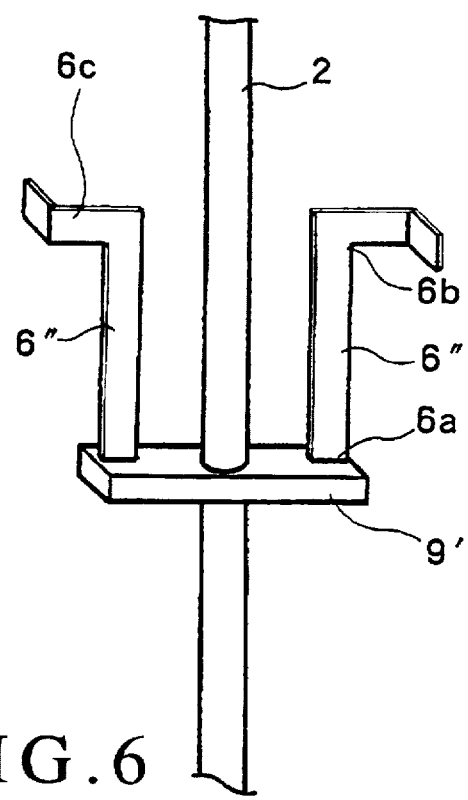
FIG. 5 is a perspective view showing a different spring member of the detector.

The fixed end 6a is rigidly coupled by means of welding to the shaft 2, or it is secured to the shaft via a sealing member. FIG. 5 shows a different example of the spring member 6. This example of spring member is constituted by leaf springs 6" or coil spring, coiled wire or the like. The spring member 6 constituted by the leaf springs 6", has one end, for instance the lower end, secured to an intermediate potion of the vibration transmission shaft 2, preferably in the neighborhood of the vibration node O, thus forming the fixed end. The free end 6b is located at a position spaced from the periphery of the vibration transmission shaft 2 and spaced axially away from the fixed end 6a. The support part 6c is formed at the free end 6c of the spring member 6. Similar to the preceding example, the spring member 6" may be secured at one end to the shaft by means of a securement member 9'. The leaf spring 6' may extend parallel to the shaft 2 or may be gradually spaced apart from the shaft 2 as in the direction toward the free end 6b.

The vibrating unit undergoes free vibrations as shown by the waveform in FIG. 6. Specifically, it undergoes free vibrations in one direction at one end of the shaft 2 (for instance on the side of the vibrator 1) (for instance the vibration node O) and in the opposite direction of the other end of the shaft 2 (for instance on the side of the detecting element 3). Commonly termed "active resonance" thus can be induced.

As a free vibration mode based on the resonance, the vibrator 1 and detecting element 3 are vibrated with a quarter wavelength from the vibration node O, as shown in FIG. 6. This is a pronounced difference from the prior art example, in which the detecting element constitutes a free vibration end.

As a modification of the structure, in which the vibrator 1 and detecting element 3 are in resonance in the vibration mode with quarter wavelength from the vibration node O, either the vibrator or the detecting element is driven in a vibration mode with one half of N (n being an integral number) wavelengths and a quarter wavelength from the node O.

As a further alternative, the vibration transmission shaft 2 may have a plurality of vibration nodes O, and the spring member 6 may be disposed at a selected one of these vibration nodes O.

The vibratory liquid detector according to the invention is applicable to a steady-state measurement of the viscosity, density or liquid level of a liquid by mounting it on a liquid tank, or on a pipe in a petroleum purifying line, or on the outer wall of a chemical reaction tank. The detecting element detects the viscosity, density, liquid level, etc. of the liquid from vibration load which changes with changes in the kind of liquid or liquid level.

The vibration transmission shaft 2 is generally a member, which extends along the vibration axis Z along which vibrations of the vibrator 1 are transmitted to the detecting element 3. The shaft may have a constant diameter throughout its length or may have an increased or reduced diameter portion.

Referring to FIGS. 1 and 2, a vibration sensor 12 is mounted on the vibration unit at the end thereof which is opposite in relation to the detecting element 3. The vibration sensor 12 detects a change in the load on the vibrator 1 while the detecting element 3 is sensing a liquid. The sensor 12 outputs a corresponding detection signal which is coupled through a lead 13 to an operational unit.

The vibration sensor 1, like the vibrator 1, includes a voltage-driven piezoelectric element, as in the prior art example described above, which converts a mechanical vibrational change (i.e., a vibration change with a change in the load applied to the detecting element 3) into a voltage signal. A voltage is applied to the vibrator 1 via a lead 14 to generate mechanical vibrations (i.e., circular vibrations based on torsional vibrations).

The vibrator 1 may include an inertial mass 15, which is provided at the end of the vibrator 1 opposite the detecting element 3 for balancing the rotational momentum of the detecting element 3 and the vibrator 1.

According to the present invention, the vibrating unit can be firmly secured by means of the spring member to a casing, a liquid vessel, or a pipe, etc. Even with this firmly secured structure, the transmission of vibrations is not spoiled, and it is possible to obtain highly reliable measurements by avoiding external disturbances caused by the suspension of the unit.

Since the spring member provides satisfactory elasticity with respect to vibrations of the vibration transmission shaft between its fixed end which is secured to an intermediate portion of the vibration transmission shaft and its free end which is spaced apart from the shaft and axially from the fixed end, vibration energy is adequately transmitted from the vibrator via the vibration transmission shaft to the detecting element. It is thus possible to provide a highly reliable liquid detector, which can adequately satisfy the conditions of suspending the vibrating unit and can induce active, steady and efficient resonance of the upper end lower portions on the vibrator side and on the detecting element side of the fixed end of the spring member. This structure is best suited as a structure for suspending the vibrating unit in order to cause resonance of the detecting element with the vibrator.

What is claimed is:

1. A viscosity detector comprising:

a vibration transmission shaft having a first end, a second end, and a central longitudinal axis;

a torsional vibrator connected to said first end of said vibration transmission shaft so as to impart a circular vibration to said vibration transmission shaft, said vibration member comprising a piezoelectric element;

a liquid detector connected to said second end of said vibration transmission shaft such that said circular vibrations from said torsional vibrator are transmitted to said liquid detector;

a spring member having a first end fixedly secured at an intermediate position of said vibration transmission shaft at a vibration node between said vibration member and said liquid detector, and a second end axially spaced from said first end and radially spaced from a peripheral surface of said vibration transmission shaft;

a support element connected to said second end of said spring member; and an inertial mass connected to said first end of said vibration transmission shaft along the central axis thereof, wherein said torsional vibrator causes said first end of said vibration transmission shaft to vibrate in one direction and said second end of said vibration transmission shaft to vibrate in the opposite direction, and said inertial mass is capable of balancing rotational momentum of said vibration member and said detector.

2. The viscosity detector as claimed in claim 1, wherein said spring member comprises a cylindrical member.

3. The viscosity detector as claimed in claim 1, wherein said spring member comprises a pair of leaf springs.

* * * * *